Figure 1:
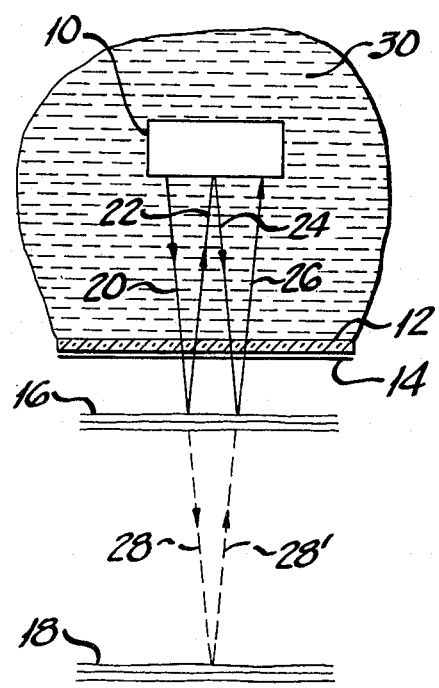

United States Patent [19]

Oakley et al.

[11] Patent Number: 4,542,745
[45] Date of Patent: Sep. 24, 1985

[54] ULTRASONIC EMULSION FLUIDS

[75] Inventors: Clyde G. Oakley, Lewistown, Pa.; Joe F. Guess, Littleton, Colo.; Cheston W. Robbins, Englewood, Colo.; Robert M. Kelly, Denver, Colo.; Dean N. Skaar, Aurora, Colo.; Stephen D. Walker, Englewood, Colo.

[73] Assignee: Technicare Corporation, Solon, Ohio

[21] Appl. No.: 508,362

[22] Filed: Jun. 27, 1983

[51] Int. Cl.[4] .............................................. B01J 13/00
[52] U.S. Cl. ....................................... 252/312; 436/8; 128/660
[58] Field of Search ................................ 128/660–663; 252/408.1, 312; 436/8

[56] References Cited

U.S. PATENT DOCUMENTS 4,277,367 7/1981 Madsen et al. ................. 128/660 X
4,391,281 7/1983 Green .................................. 128/660

OTHER PUBLICATIONS

Edmonds, P. D. et al., "A Human Abdominal Tissue Phantom", *Ultrasonic Tissue Characterization II*, M. Linzer ed., NBS Spec. Publ., 525, US GPO, Wash., D.C., 1979.

Allegra, Jr. et al., "Attenuation of Sound in Suspension and Emulsion: Theory & Exp.", J. Acoust. Soci. Amer., vol. 51, No. 5, (1972), pp. 1545–1564.

*Primary Examiner*—Kyle L. Howell
*Assistant Examiner*—Francis J. Jaworski
*Attorney, Agent, or Firm*—W. Brinton Yorks, Jr.

[57] ABSTRACT

An ultrasonic emulsion fluid is provided for use in ultrasonic probes of medical ultrasonic diagnostic systems, in which the fluid couples ultrasonic energy between a transducer and human tissue. The emulsion outer phase is a water and velocity enhancer mixture. Suitable enhancers include alcohols such as ethylene glycol, propylene glycol, or glycerol. The suspended phase of the emulsion is an oil phase such as a silicone fluid. The silicone fluid droplets in the emulsion exhibit an average size which provides the emulsion with desired attenuation characteristics over a given band of ultrasonic frequencies.

16 Claims, 7 Drawing Figures

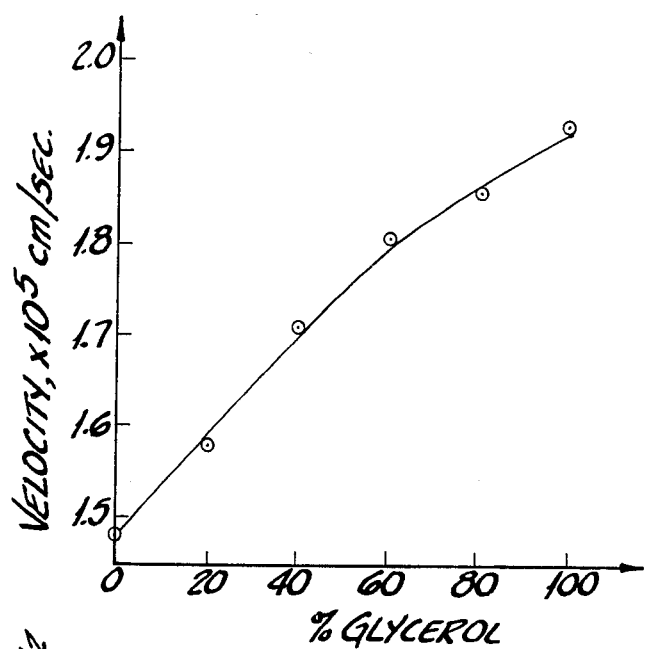
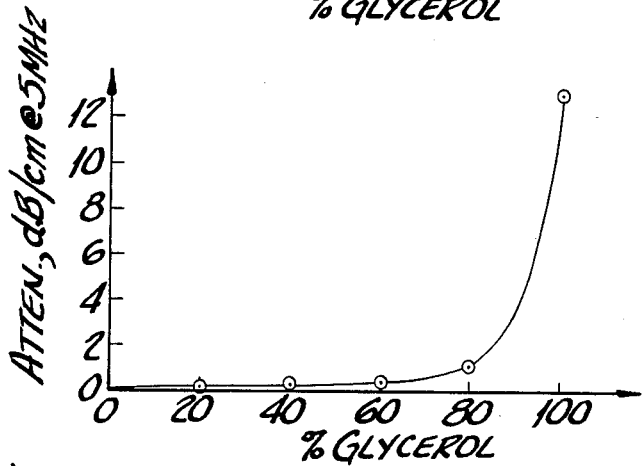
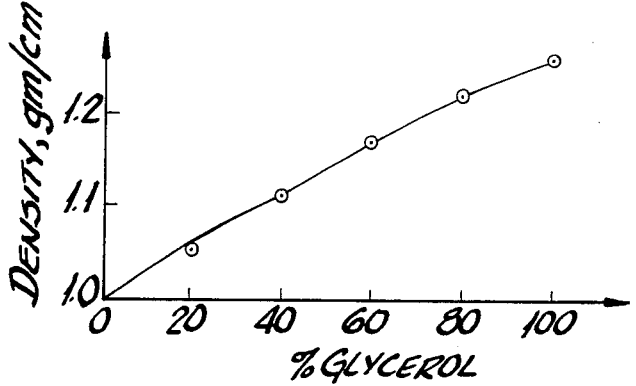

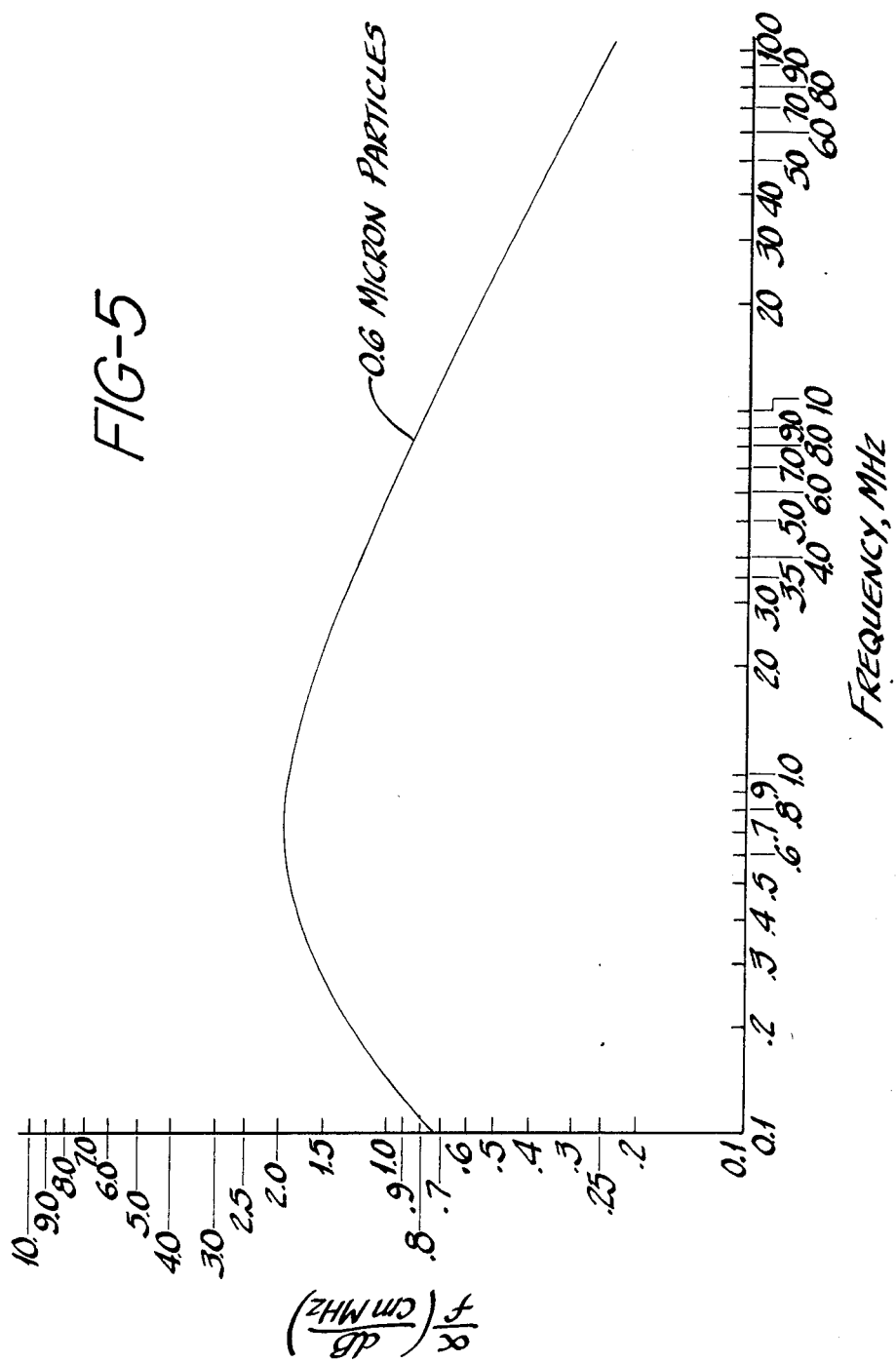

ULTRASONIC EMULSION FLUIDS

This invention relates to ultrasonic fluids and, in particular, to ultrasonic emulsion fluids which are transmissive to ultrasonic energy in many similar respects as human tissue.

Ultrasonic fluids are commonly used in ultrasonic probes of ultrasonic diagnostic imaging systems. An ultrasonic probe is a hand-held unit containing an ultrasonic transducer for transmitting and receiving ultrasonic energy to and from the body of a patient. Many probes, such as the sector probe described in U.S. Pat. No. 4,330,874, mechanically oscillate the ultrasonic energy beam to create a sector image of the patient's tissue. The beam may be oscillated by oscillating the transducer, or as in the case of the sector probe described in the aforesaid U.S. patent, by oscillating a mirror which reflects energy between a fixed transducer and the patient.

The oscillating element of the mechanical probe system cannot be surrounded by air, since ultrasonic energy is not smoothly transmitted by air. Rather, an ultrasonic fluid completely fills the volume through which the ultrasonic energy passes between the patient's skin line and the transducer. An ultrasonically transparent aperture or membrane seals the fluid compartment of the probe at the skin line. The oscillating element then moves in a fluid bath which smoothly transmits ultrasonic beams into the tissue of the patient and back again.

The ultrasonic fluid has numerous characteristics which can affect the performance of the ultrasonic imaging system. The composition of the fluid will affect the velocity of the ultrasonic signals as they pass through the fluid. It is desired that the ultrasonic velocity be closely matched to the velocity of ultrasonic signals in the human body. This is because the aperture which seals the fluid compartment at the skin line is often curved. If the ultrasonic velocity changes at this curved surface, the aperture would effectively function as an acoustic lens, producing defocusing effects in the ultrasound image.

Another important characteristic of the fluid is its acoustic impedance. Ideally, the impedance at the face of the transducer should match the impedance of human skin. The ultrasonic fluid should likewise have the same impedance to acoustically couple the transducer to the body. Under less than ideal circumstances it is desirable for the acoustic impedance of the fluid to closely match the impedance of the skin. A sharp impedance mismatch will cause reflections of ultrasonic signals at the skin line, thereby producing reverberation in the ultrasound images.

A third important characteristic of the fluid is its attenuation characteristic. It is desirable for ultrasonic signals to pass through the fluid without severe attenuation which would sharply degrade the signal-to-noise ratio of the received ultrasonic echo signals. But it is also desirable for the fluid to substantially attenuate unwanted reverberation and multiply reflected signals. Moreover, it is desirable that the attenuation characteristic of the fluid be independent of frequency. The ultrasonic energy produced by the transducer is not monotonic, but occupies a band of frequencies. It is desirable that signal frequencies within the band be equally attenuated by the fluid.

Finally, the viscosity of the fluid is important in several respects. When the ultrasonic fluid is an emulsion, it is desirable to have a highly viscous fluid which will retain the suspended material in its emulsified state. But it is also desirable to have a viscosity which is low enough to prevent the suspension of air bubbles in the fluid which would result in signal scattering. Air bubbles which form in the fluid should preferably float rapidly to the top of the fluid chamber and out of the path of the ultrasonic signals.

In accordance with the principles of the present invention, an ultrasonic emulsion fluid is provided which possesses many of the more desirable characteristics discussed above. The emulsion outer phase is a water and velocity enhancer mixture. Suitable enhancers include alcohols such as ethylene glycol, propylene glycol, or glycerol. The suspended phase of the emulsion is an oil phase such as a silicone fluid. The silicone fluid droplets in the emulsion exhibit an average size which provides the emulsion with desired attenuation characteristics over a given band of ultrasonic frequencies.

Figure 2:
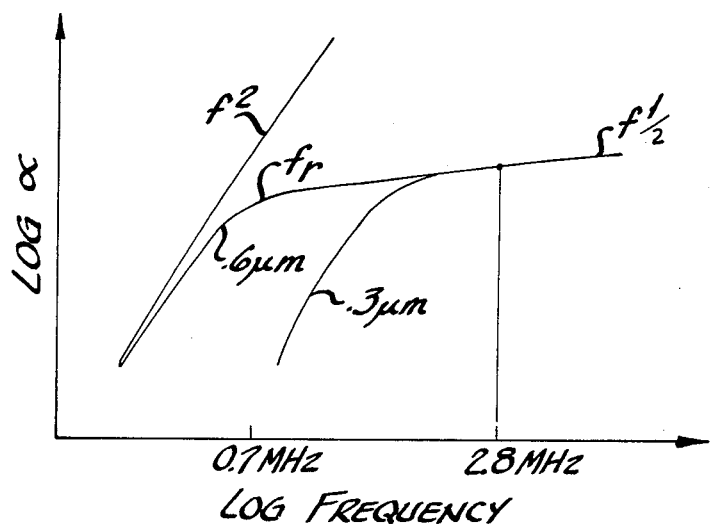
Figure 4:
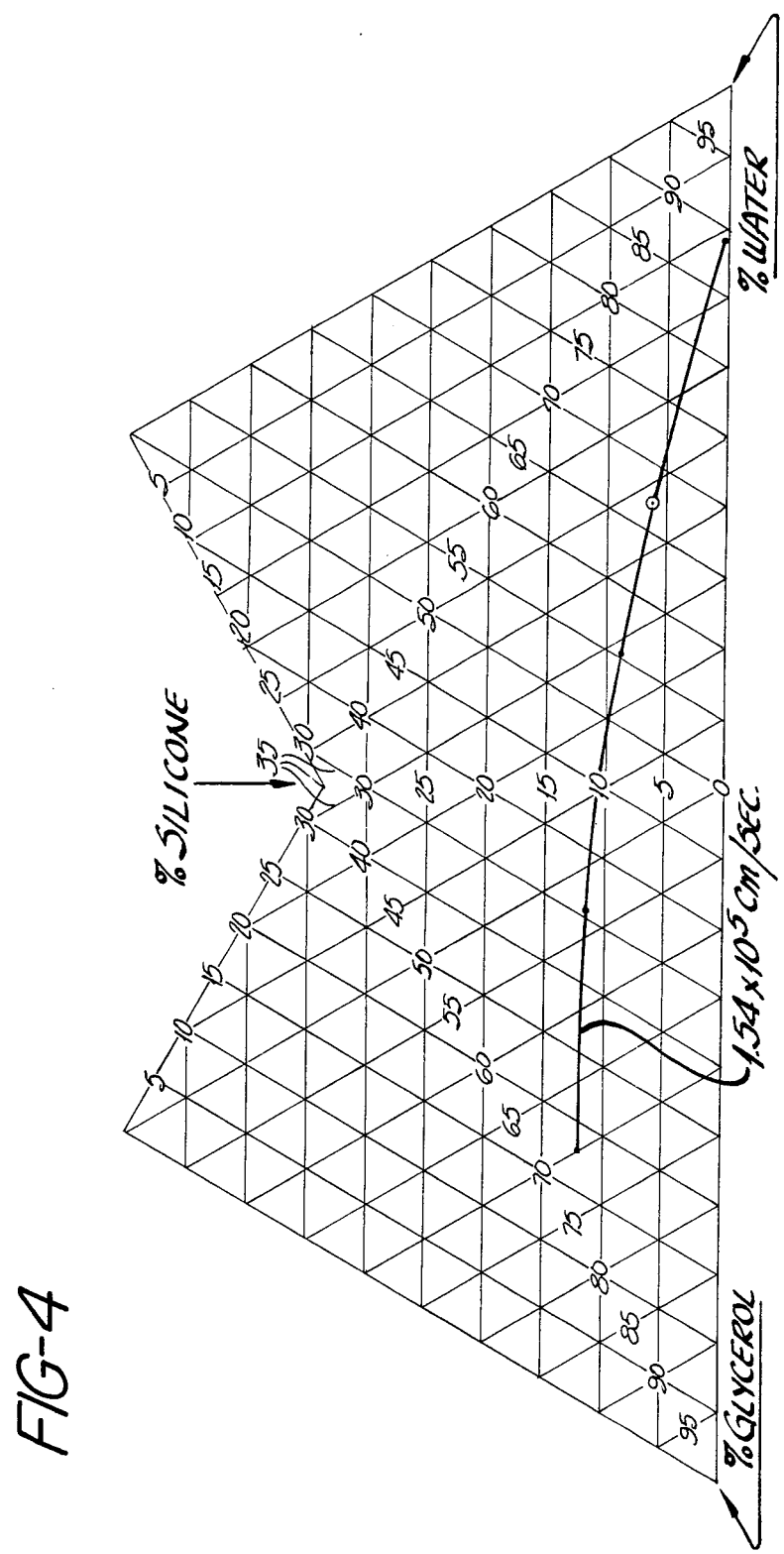

In the drawings:

FIG. 1 illustrates the effect of a multiply reflected ultrasound signal;

FIG. 2 graphically represents the attenuation characteristics of an ultrasonic emulsion fluid of the present invention as a function of frequency;

FIGS. 3A–3C graphically illustrate several of the acoustic properties of a glycerol enhancer;

FIG. 4 illustrates a constant velocity profile of a silicone, water and glycerol emulsion; and FIG. 5 is an attenuation versus frequency plot for a suspension of 0.6 micron silicone droplets in water.

From their base of experience in working with ultrasonic fluids, the present inventors determined that desirable ultrasonic fluids must exhibit relatively high attenuative properties to reduce the effects of multiply scattered signals. An example of an effect of multiply scattered signals is shown in FIG. 1. A transducer 10 is located in a chamber of ultrasonic fluid 30. The chamber is sealed by an ultrasonically transparent membrane 12, which is pressed against the skin line 14 of a patient. It is desired to ultrasonically image a tissue layer 16 in the body of the patient.

The transducer 10 transmits a beam of ultrasonic energy along a path 20. A portion of the energy is reflected by the tissue layer 16 and returns to the transducer 10 along a path 22. The reflected echo signal is received by the transducer 10 and the length of the paths 20 and 22, as measured by the transmit-to-receive time, is used to produce an image of the tissue layer 16.

System operation would be satisfactory if the process ended at this point. However, due to impedance mismatches between the ultrasonic fluid 30 and the face of the transducer 10, the ultrasonic signal can again be reflected at the point of return of the first echo. The second reflection will follow path 24 back to the tissue layer 16, be reflected again, and return to the transducer 10 along path 26.

The imaging system cannot recognize the reflective process by which the final echo signal arrived; it can only determine the time between transmission and reception. Hence, the system will form an image on the basis of the total length of paths 20, 22, 24 and 26. That image will be the apparent image layer 18, since the system will deduce that the doubly reflected signal traversed paths 20, 28, 28' and 26.

Such doubly reflected signal images can be prevented by using an attenuative ultrasonic fluid which significantly attenuates signals that travel four times between the transducer 10 and the membrane 12. These signals should desirably be attenuated to levels which are below the sensitivity threshhold of the system. The attenuative characteristic of the fluid can also aid in the elimination of many randomly scattered signal echoes which traverse substantial path lengths through the fluid. The reception of these scattered signals produces "fog" in the image.

However, the attenuative characteristics of many fluids vary as a function of frequency, with higher frequency signals experiencing increased attenuation. The doubly reflected, multipath signals are generally low frequency signals, and a fluid which is capable of strongly attenuating these signals can even more greatly attenuate valid high frequency signals. Elimination of high frequency signal components can degrade the resolution of the ultrasound image. Thus, it is desirable to provide an ultrasonic fluid which exhibits a low frequency dependence of attenuation that will not eliminate valid high frequency signals.

It was decided to use an emulsion of an oil phase suspended in a water phase for the ultrasonic fluid of the present invention, since many of the desired properties of an ultrasonic fluid can be controllably varied in an emulsion. In particular, emulsions exhibit attenuative properties to ultrasound which are governed by several recognizable mechanisms. The primary attenuation mechanism of the emulsion of the present invention is the thermal loss mechanism.

Thermal losses result when the ultrasonic waves impact the surfaces of the suspended particles and some of the ultrasonic energy is converted to heat in the form of a thermal wave. For ultrasonic waves of a given frequency the thermal losses are a function of the size of the suspended particles, and are described in terms of the thermal wave. The ultrasonic wave consists of alternate regions of compression and rarefaction that move through the medium at the sound velocity. During compression the temperature of the medium is increased and is decreased during the rarefaction phase of the wave. The amount by which the temperature changes is proportional to the factor $\beta/(\rho C\rho)$, where $\beta$ is the volumetric thermal expansion coefficient, $\rho$ is the density and $C\rho$ is the specific heat of the material. A droplet of oil suspended in water will experience greater temperature changes than the water because this factor is larger for the oil. As a compression phase of the wave passes through the emulsion, for example, the droplet is suddenly warmer than the surrounding medium and heat begins conducting from the droplet to the water, thereby dissipating energy. One-half cycle later the rarefaction phase passes through the emulsion, and since the droplet is cooler than the surrounding water, heat begins to flow from the water to the droplet, again dissipating energy. The result of both phases is a thermal wave propagating from the surface of the suspended droplet, which has a wavelength inversely proportional to the square root of the frequency, since the thermal wave is a diffusion type wave.

Thermal losses are a function of the size of the suspended particle. When the thermal wavelength is comparable in size to the suspended particle, the whole sphere participates in the loss mechanism and maximum attenuation by conversions to thermal waves occurs. For thermal conduction at low frequencies the temperature difference between the particle and the suspending fluid will equilibrate in the time of passage of a sound wave, whereas at high frequencies only a small portion of the particle volume near the surface is involved in the thermal conduction process.

Suspended particles have a critical frequency at which the thermal wavelength is equal to the particle diameter, and which is inversely proportional to the square of the radii of the suspended particles. As particle size is increased the critical frequency decreases, and as the particles get smaller, the critical frequency gets higher. Furthermore, there is a marked difference in frequency dependence of attenuation depending on the frequency of the ultrasonic waves. As the ultrasonic frequency increases from low frequencies toward the critical frequency the attenuation increases in proportion to $f^2$, since the thermal energy has time to equilibrate between ultrasonic waves and the system is approaching the maximal condition when the whole sphere participates in the loss mechanism. But when the ultrasonic frequencies are above the critical frequency, the attenuation changes with frequency in proportion to $f^1$, since the thermal wave does not have time to equilibrate between ultrasonic waves and only the near surface volume of the particles participates in the energy exchange. Therefore, it is desirable to utilize a suspension of particles which are large enough to have a critical frequency below the ultrasonic frequencies of operation, yet small enough to be stable in suspension without settling.

A number of materials in solution were initially considered for the ultrasonic fluid. Divalent salts were considered, but high concentrations would be required. Their acoustic impedances were undesirable and the salts were known to attack certain metals. Acetic acid was considered but again, high concentrations were required, and the acoustic impedance and corrosive properties were undesirable. Finally, oil in water emulsions were chosen due to their controllable frequency dependence, velocity and attenuation. Such emulsions also do not deteriorate the materials with which they are likely to come in contact.

Several oil candidates were examined. It was found that mineral oil was not stable enough in suspension, and that a high concentration was required (30%) to afford the desired acoustic properties. Silicone fluid was examined and found to be more desirable, with low concentrations providing the desired characteristics for the emulsion. The silicone fluid used in the preferred emulsion is Dow Corning dimethyl siloxane polymer. This commercially available silicone fluid is available in a range of viscosities, is not water soluble, is nontoxic, and has a wide range of industrial uses. Type Dow Corning 346 fluid was used, which is a composition of approximately 60% Dow Corning 200 (350 centistokes) silicone, 40% water, and small amounts of Triton W-30 and Tergitol TMN-6 stabilizer.

As discussed above, it is desirable for the suspended particles to be large enough to afford a relatively low critical frequency while remaining stable in suspension. The present inventors have found acceptable droplet sizes over the range of 0.15 microns to 1.5 microns, with droplets in the preferred emulsion exhibiting a droplet size of 0.6 microns and a critical frequency of approximately 0.7 MHz. A comparision of the attenuative characteristics of 0.6 and 0.3 micron particles with a $f^2$ reference line is shown in FIG. 2.

The preferred ultrasonic emulsion fluid is prepared so as to control the ultrasonic velocity, the acoustic impedance, and the attenuation of the emulsion. The present inventors have found that due to the low bulk modulus of the silicone fluid and water, the acoustic velocity of the oil and water emulsion is lower than desired. The acoustic velocity in human tissue is $1.54 \times 10^5$ cm/sec. The velocity in water is $1.48 \times 10^5$ cm/sec., and the acoustic velocity in silicone fluids is even less. Thus a velocity enhancing additive is necessary to bring the acoustic velocity of the emulsion up to the velocity in human tissue.

The velocity, density and impedance values for silicone and water hence can be calculated analytically using the expressions $$B = c^2 \rho$$

$$Z = \rho c$$

for the bulk modulus (B) and impedance (Z), where c is the velocity and $\rho$ is the density. Using these basic expressions, the following relationships are derived from velocity, density and impedance of the oil (o) and water (w) phases:

$$c = \sqrt{\frac{\left(\frac{M_w}{\rho_w} + \frac{M_o}{\rho_o}\right)^2}{\left(\frac{M_w}{\rho_w B_w} + \frac{M_o}{\rho_o B_o}\right)(M_w + M_o)}} \quad \rho = \frac{1}{\frac{M_w}{\rho_w} + \frac{M_o}{\rho_o}}$$

$$Z = \sqrt{\frac{1}{\frac{M_w}{\rho_w \rho_w} + \frac{M_o}{\rho_o B_o}}}$$

M indicates the ratio of the mass of the particular phase to the total mass.

It was decided to consider alcohol solutions as velocity enhancers. Three glycols, ethylene glycol, propylene glycol, and glycerol were selected for examination. The acoustic properties of these substances were measured and represented graphically, since they are nonlinear and do not lend themselves to analytical expression. All three substances were found to enhance acoustic velocity, but ethylene glycol and propylene glycol have lower densities which do not significantly increase the emulsion density. It was therefore decided to use glycerol as the enhancer, since glycerol raises both the acoustic velocity and the density of the emulsion to desirable levels. The increase in density is significant because the impedance of the oil and water phase alone is lower than desired. Since impedance is equal to the product of density and velocity, the higher density and velocity of glycerol was found to improve the impedance of the emulsion nearly to that of human skin, which is $1.7 \times 10^5$ gm/cm$^2$ sec. The measured characteristics of glycerol are shown in FIG. 3.

By picking interpolated points from the graphs of FIGS. 3A–3C and using the above equations, constant velocity profiles can be constructed for the silicone, water and glycerol emulsion. Such a profile is shown in FIG. 4 for the desired human tissue velocity of $1.54 \times 10^5$ cm/sec. The constant velocity profile is used in preference to an impedance plot because it is desired to control velocity more tightly than impedance to minimize refraction and defocusing effects. Small signal reflections due to an imprecise impedance matching can be eliminated by the attenuative characteristics of the emulsion.

The attenuation of the chosen 0.6 micron size silicone particles is then calculated for the thermal loss mechanism of fluid particles in water using the expressions developed in the article "Attenuation of Sound in Suspension and Emulsion: Theory and Experiments", by Allegra and Hawley, Journ. Acoust. Soc. of America, Vol. 51, No. 5 (Part 2) (July, 1971). These attenuation calculations are represented graphically in FIG. 5. The illustrated attenuation characteristics shown in FIG. 5 are for a 7.94% concentration of DC-200 silicone fluid with a 350 centistoke viscosity and 0.6 micron particle size. At the ultrasonic center frequency of 3.5 MHz, the attenuation is seen to be 1.25 dB/cm MHz. From considerations of the ultrasonic path lengths in the scan head in which the emulsion is to be used, it was decided that a preferred attenuation was 1.0 dB/cm MHz. Since the attenuation is approximately proportional to the amount of silicone in the emulsion at these low proportions, a linear interpolation of the desired and graphical values produced a calculated concentration of 6% silicone fluid for the desired attenuation value. Returning to the constant velocity profile of FIG. 4 and finding the 6% point on the constant velocity curve, the necessary proportion of glycerol and water in the emulsion may be found directly from the graph. The 6% point is the circled dot on the curve of FIG. 4.

The emulsion prepared in accordance with the foregoing technique was comprised of 6% silicone fluid, 26.5% glycerol, and 67.5% water. Its characteristics were measured and were found to be: attenuation, 3.22 dB/cm at 3.5 MHz; velocity, $1.535 \times 10^5$ cm/sec; density, 1.066 gm/cm$^3$; and impedance, $1.636 \times 10^5$ gm/cm$^2$ sec. The emulsion was then tested to determine factors such as frequency dependence, acoustic stability over time, emulsion stability, and material compatibility. The emulsion proved to be satisfactory in all of the examined criteria, particularly stability, an important criterion for ultrasonic emulsion fluids. It was found that the 0.6 micron particles were not quite small emough to remain in suspension indefinitely through thermal agitation alone, but that the motion of the moving member of the scanning system (i.e., the oscillating mirror in the test scan head) provided more than sufficient agitation to keep the silicone particles in suspension during use. It was further noted that the low viscosity of the novel fluid (50 centistokes) allowed bubbles to rapidly float to the top of the ultrasonic fluid chamber and out of the beam path.

What is claimed is:

1. An ultrasonic emulsion fluid suitable for use in an ultrasonic probe for coupling ultrasonic energy between an ultrasonic transducer and human tissue comprising:

a suspended oil phase of droplets exhibiting an average diameter in the range of 0.15 microns to 1.5 microns for providing a given attenuation characteristic to ultrasound over a predetermined band of ultrasonic frequencies; and an emulsion outer phase of water and a velocity enhancer, said velocity enhancer being chosen so that the velocity of ultrasound in said fluid will closely approximate the velocity of ultrasound in human tissue.

2. An ultrasonic emulsion fluid suitable for use in an ultrasonic probe for coupling ultrasonic energy between an ultrasonic transducer and human tissue comprising:
- a suspended oil phase of droplets exhibiting an average diameter chosen to provide said fluid with an attenuation characteristic which varies approximately in proportion to $f^{\frac{1}{2}}$ as a function of frequency (f) over the band of frequencies of said ultrasonic energy; and
- an emulsion outer phase of water and a velocity enhancer, said velocity enhancer being chosen so that the velocity of ultrasound in said fluid will closely approximate the velocity of ultrasound in human tissue.

3. The ultrasonic emulsion fluid of claim 2, wherein said suspended oil phase comprises a silicone fluid.

4. The ultrasonic emulsion fluid of claim 3, wherein the average diameter of said silicone fluid droplets is in the range of 0.15 microns to 1.5 microns.

5. The ultrasonic emulsion fluid of claim 4, wherein the average diameter of said silicone fluid droplets is approximately 0.6 microns.

6. The ultrasonic emulsion fluid of claim 3, wherein the addition of said velocity enhancer to said fluid increases both the acoustic velocity and the density of said fluid.

7. The ultrasonic emulsion fluid of claim 3, wherein said velocity enhancer is one of the substances ethylene glycol, propylene glycol, and glycerol.

8. The ultrasonic emulsion fluid of claim 6, wherein said velocity enhancer comprises glycerol.

9. The ultrasonic emulsion fluid of claim 3, wherein the percentage of said emulsion fluid comprising silicone fluid is 12% or less.

10. The ultrasonic emulsion fluid of claim 9, wherein said velocity enhancer comprises glycerol, and said emulsion fluid comprises 6% silicone fluid, 26.5% glycerol, and 67.5% water.

11. The ultrasonic emulsion fluid of claim 8, wherein the viscosity of said emulsion fluid is approximately 50 centistokes.

12. The ultrasonic emulsion fluid of claim 1, wherein said suspended oil phase comprises a silicone fluid.

13. The ultrasonic emulsion fluid of claim 12, wherein the average diameter of said silicone fluid droplets is approximately 0.6 microns.

14. The ultrasonic emulsion fluid of claim 12, wherein said velocity enhancer is one of the substances ethylene glycol, propylene glycol, and glycerol.

15. The ultrasonic emulsion fluid of claim 14, wherein said velocity enhancer comprises glycerol.

16. The ultrasonic emulsion fluid of claim 15, wherein said emulsion fluid comprises 6% silicone fluid, 26.5% glycerol, and 67.5% water.

* * * * *